United States Patent
Engwall et al.

(10) Patent No.: US 11,020,616 B2
(45) Date of Patent: Jun. 1, 2021

(54) DETERMINING A DISTRIBUTION OF SPOTS OF VARYING SIZES FOR ION BEAM THERAPY USING OPTIMIZATION

(71) Applicant: RaySearch Laboratories AB, Stockholm (SE)

(72) Inventors: Erik Engwall, Hägersten (SE); Lars Glimelius, Stockholm (SE); Martin Janson, Enskededalen (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 16/625,871

(22) PCT Filed: Jun. 26, 2018

(86) PCT No.: PCT/EP2018/067058
§ 371 (c)(1),
(2) Date: Dec. 23, 2019

(87) PCT Pub. No.: WO2019/002261
PCT Pub. Date: Jan. 3, 2019

(65) Prior Publication Data
US 2020/0129781 A1    Apr. 30, 2020

(30) Foreign Application Priority Data
Jun. 28, 2017    (EP) .................................... 17178291

(51) Int. Cl.
*A61N 5/10*    (2006.01)
(52) U.S. Cl.
CPC ......... *A61N 5/1031* (2013.01); *A61N 5/1043* (2013.01); *A61N 2005/1087* (2013.01)

(58) Field of Classification Search
CPC ................ A61N 5/1031; A61N 5/1043; A61N 2005/1087; A61N 2005/1032; A61N 2005/1034; A61N 2005/1035
See application file for complete search history.

(56) References Cited

U.S. PATENT DOCUMENTS

2004/0104354 A1    6/2004    Haberer et al.
2009/0189095 A1*   7/2009    Flynn ....................... A61N 5/10
                                                              250/492.3
(Continued)

FOREIGN PATENT DOCUMENTS

EP              2579265 A1    4/2013
WO    WO-2008106483 A1    9/2008

*Primary Examiner* — Sean M Luck
(74) *Attorney, Agent, or Firm* — Faegre Drinker Biddle & Reath LLP (57) ABSTRACT

According to a first aspect, it is presented a method for determining a treatment plan comprising a distribution of spots for use with ion beam therapy for providing the spots in a target volume. The method comprises the steps of: selecting energy layers to be used in the treatment plan; determining a number of spot sizes to use; generating, for each energy layer, one copy of the energy layer for each spot size to use and populating each copy with spots of the spot size for that copy; optimizing spots of all copies of all energy layers, by repeatedly varying a weight of at least a subset of the spots and calculating an effect on a performance measurement, wherein the performance measurement is calculated by combining a plurality of evaluation criteria, comprising a first criterion related to total treatment time and a second criterion related to a desired dose distribution.

11 Claims, 4 Drawing Sheets

(56) References Cited

U.S. PATENT DOCUMENTS

| | | | |
|---|---|---|---|
| 2010/0006778 A1* | 1/2010 | Flynn | A61N 5/10 250/492.3 |
| 2011/0108737 A1 | 5/2011 | Pu et al. | |
| 2015/0090894 A1 | 4/2015 | Zwart et al. | |
| 2017/0036037 A1* | 2/2017 | Luan | A61N 5/1001 |

* cited by examiner

DETERMINING A DISTRIBUTION OF SPOTS OF VARYING SIZES FOR ION BEAM THERAPY USING OPTIMIZATION

This application is the national stage application under 35 U.S.C. § 371 of International Application No. PCT/EP2018/067058, filed on Jun. 26, 2018, and claims benefit of European Patent Application No. 17178291.5, filed on Jun. 28, 2017, both of which are incorporated herein by reference in their entirety.

TECHNICAL FIELD

The invention relates to a method, a treatment planning system, a computer program and a computer program product for distribution of spots of varying sizes for use with ion beam therapy for providing the spots in a target volume.

BACKGROUND

In ion beam therapy, a beam of ions (e.g. protons or heavier ions) is directed towards a target volume. The target volume can e.g. represent a cancer tumor. The particles penetrate the tissue and deliver a dose of energy to induce cell death. An advantage of ion beam therapy is that there is a significant peak in the dose distribution, known as a Bragg peak. The Bragg peak is a peak of dose delivery occurring at a certain depth, after which the dose delivery falls of quickly. This can be compared with electron beam therapy or X-ray therapy where the maximum dose always occurs at shallow depth and distal dose fall-off cannot be controlled with the same sharp fall-off as for ion therapy.

The depth of the Bragg peak in the patient can be controlled by adjusting the kinetic energy of the particles. Lateral position can be controlled using electromagnets to deflect the focused beam. This allows for delivery of highly localized doses at well-controlled positions in the patient. The dose delivered from a certain combination of kinetic energy, and lateral deflection of the beam is referred to as a spot. The number of particles delivered to a spot is commonly referred to as the spot weight. By providing spots in many different locations in a three-dimensional space, the target volume can be covered with the desired dose distribution. The kinetic energies of the spots are often, but not necessarily, distributed over a number of discrete energies. A group of spots with the same kinetic energy, but different lateral deflection is often referred to as an energy layer. This procedure is called active scanning ion beam therapy, also known as pencil beam scanning.

The planning of how the spots should be delivered is performed in a treatment planning system. The treatment planning system determines the energy layers to be used and the distribution and weights of spots therein, but the treatment planning system does not deliver the ion beam. This is done by an ion beam system, to which the treatment planning system is connected in a known way. The size of the spots for a given setup and a given position in the patient is dictated by the ion beam system. The spot size is often fixed for a certain energy, but some ion beam systems do allow for control of the spot size in the lateral directions in the same energy layer. The machine setting to obtain a certain spot size for an energy layer may be referred to as a spot size setting.

It is a complex task to determine the distribution of spots in relation to the target volume and the surrounding healthy tissue. The possibility to adjust the spot size, makes this task even more complex.

SUMMARY

It is an object to improve how spots are distributed in and around a target volume, when the size of the spots can be adjusted.

According to a first aspect, it is presented a method for determining a treatment plan comprising a distribution of spots of varying sizes for use with ion beam therapy for providing the spots in a target volume, wherein each spot represents a collection of ions of a specific energy and of a specific spot size at a specific lateral location. The method is performed in a treatment planning system and comprises the steps of: selecting energy layers to be used in the treatment plan; determining a number, greater than one, of spot sizes to use; generating, for each energy layer, one copy of the energy layer for each spot size to use and populating each copy with spots of the spot size for that copy; optimizing spots of all copies of all energy layers, by repeatedly varying a weight, related to the number of ions that are delivered to the spot, of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved.

The step of optimizing may comprise performing a spot filtering to remove spots with weights below a threshold value.

The method may further comprise the step, after the step of optimizing spots, of: finding any multi spot size region of a single energy layer which is covered by spots of different sizes of respective copies of the energy layer; determining, in each multi spot size region, which single spot size to keep and removing the spots of other spot sizes in the multi spot size region; and returning to the step of optimizing spots.

The method may further comprise the step, after the step of determining which spot size to keep, of: adding, in each multi spot size region when the spot size to keep is not the largest spot size in the multi spot size region, spots of the spot size to keep, to improve coverage.

The step of determining which spot size to keep may comprise determining to keep a spot size according to a user parameter.

The second criterion may improve the performance measurement when a penumbra outside the target volume is reduced.

According to a second aspect, it is presented a treatment planning system for determining a treatment plan comprising a distribution of spots of varying sizes for use with ion beam therapy for providing the spots in a target volume, wherein each spot represents a collection of ions of a specific energy level and of a specific spot size at a specific lateral location. The treatment planning system comprises: a processor; and a memory storing instructions that, when executed by the processor, cause the treatment planning system to: select energy layers to be used in the treatment plan; determine a number, greater than one, of spot sizes to use; generate, for each energy layer, one copy of the energy layer for each spot size to use and populating each copy with spots of the spot size for that copy; and optimize spots of all copies of all energy layers, by repeatedly varying a weight, related to the number of ions that are delivered to the spot, of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved.

The treatment planning system may further comprise instructions that, when executed by the processor, cause the treatment planning system to: find any multi spot size region of a single energy layer which is covered by spots of different sizes of respective copies of the energy layer; determine, in each multi spot size region, which single spot size to keep and removing the spots of other spot sizes in the multi spot size region; and return to the instructions to optimize spots.

The treatment planning system may further comprise instructions that, when executed by the processor, cause the treatment planning system to: add, in each multi spot size region when the spot size to keep is not the largest spot size in the multi spot size region, spots of the spot size to keep, to improve coverage.

The instructions to determine which spot size to keep may comprise instructions that, when executed by the processor, cause the treatment planning system to determine to keep a spot size according to a user parameter.

The second criterion may improve the performance measurement when a penumbra outside the target volume is reduced.

According to a third aspect, it is presented a treatment planning system for determining a treatment plan comprising a distribution of spots of varying sizes for use with ion beam therapy for providing the spots in a target volume, wherein each spot represents a collection of ions of a specific energy level and of a specific spot size at a specific lateral location. The treatment planning system comprises: means for selecting energy layers to be used in the treatment plan; means for determining a number, greater than one, of spot sizes to use; means for generating, for each energy layer, one copy of the energy layer for each spot size to use and populating each copy with spots of the spot size for that copy; means for optimizing spots of all copies of all energy layers, by repeatedly varying a weight, related to the number of ions that are delivered to the spot, of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved.

According to a fourth aspect, it is presented a computer program for determining a treatment plan comprising a distribution of spots for use with ion beam therapy for providing the spots in a target volume, wherein each spot represents a collection of ions of a specific energy level and of a specific spot size at a specific lateral location. The computer program comprises computer program code which, when run on a treatment planning system causes the treatment planning system to: select energy layers to be used in the treatment plan; determine a number, greater than one, of spot sizes to use; generate, for each energy layer, one copy of the energy layer for each spot size to use and populating each copy with spots of the spot size for that copy; optimize spots of all copies of all energy layers, by repeatedly varying a weight, related to the number of ions that are delivered to the spot, of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved.

According to a fifth aspect, it is presented a computer program product comprising a computer program according to the fourth aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

According to embodiments presented herein, a distribution of spots of varying sizes using ion beam therapy is determined. This is accomplished by creating, for each layer, one copy of the layer for each spot size, after which optimization is performed. The criteria for the optimization are set such that both a short treatment time and a desired dose distribution is preferred. The optimization will then result in spots of appropriate sizes at different locations of each energy layer.

Figure 1:
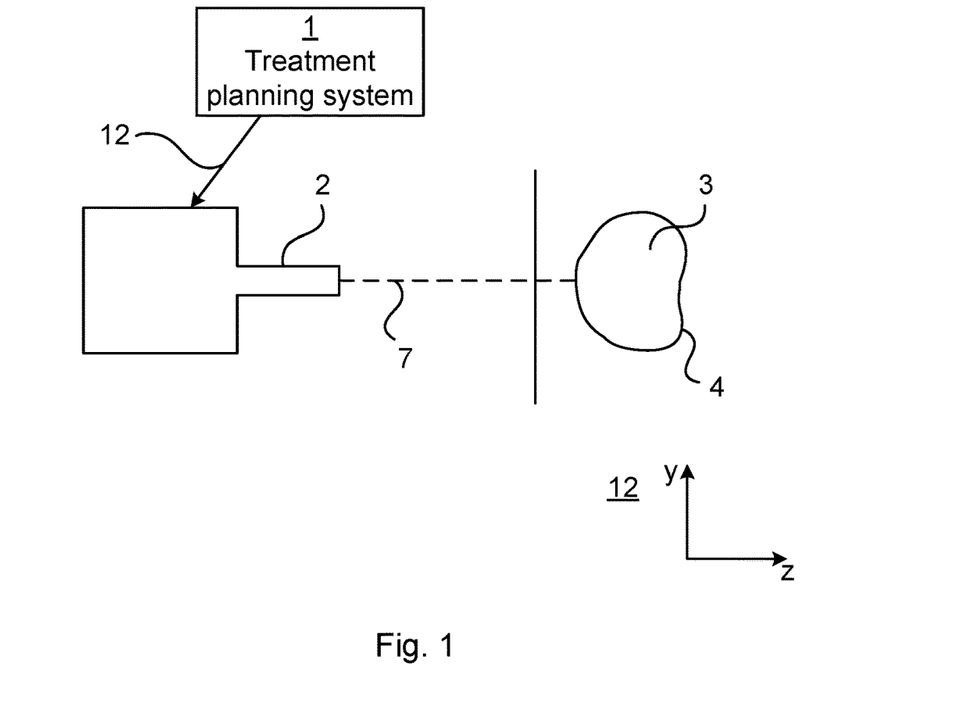
FIG. 1 is a schematic drawing illustrating an environment in which embodiments presented herein can be applied.

FIG. 1 is a schematic drawing illustrating an environment in which embodiments presented herein can be applied. A treatment planning system 1 determines a distribution of spots for ion beam therapy. This is communicated as a spot distribution data set 12 to an ion beam system 2. Based on the spot distribution data set, the ion beam system 2 generates an ion beam 7 for providing spots to a target volume 3 of a patient. The target volume 3 is delimited by an edge 4.

In a coordinate system, the depth is represented along a z-axis and the y-axis is upwards in FIG. 1. The view in FIG. 1 can thus be considered to be a side view. The location of the spot depth wise, i.e. the position along the z-axis, is controlled by the energy of the ions; higher energy results in a deeper location of the spot. Moreover, the lateral position, along the y-axis and x-axis (not shown in FIG. 1), is controlled using electromagnets to deflect the beam 7. In this way, spots can be spots can be provided to achieve a dose distribution covering the target volume 3 in three dimensions.

Figure 2:
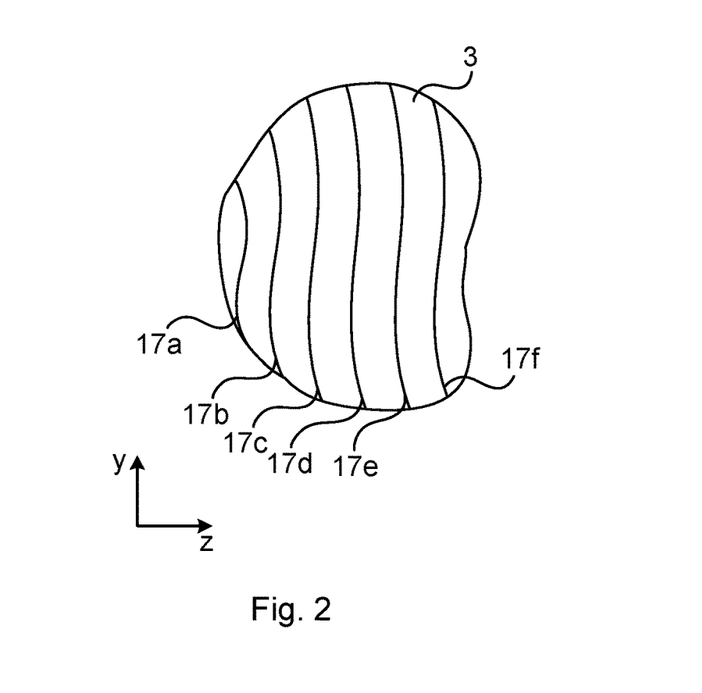
FIG. 2 is a schematic drawing illustrating Bragg peak depths of energy layers in the target volume of FIG. 1.

FIG. 2 is a schematic drawing illustrating energy layers of the target volume 3 of FIG. 1. FIG. 2 is a side view, from the same perspective as the view of FIG. 1. As explained above, the depth (z-direction) of the Bragg peak depends on energy level. Here, there are six energy levels shown 17a-f in the target volume 3. The energy levels indicate where the Bragg peaks occur for ions at different lateral locations but of the same energy. For instance, a first energy level 17a shows where the Bragg peaks occur when ions of a first amount of energy are supplied using the ion beam therapy in the system of FIG. 1. A second energy level 17b shows where the Bragg peaks occur when ions of a second amount of energy are supplied, etc. It is to be noted that the geometry, density, and material composition of tissue that the ion beam passes through affects the depth. For instance, if the beam passes through bone, this results in a different depth of the Bragg peak than if the beam passes through muscle tissue. Consequently, each energy level 17a-f does not need to be a straight line of a certain depth.

Figure 3A:
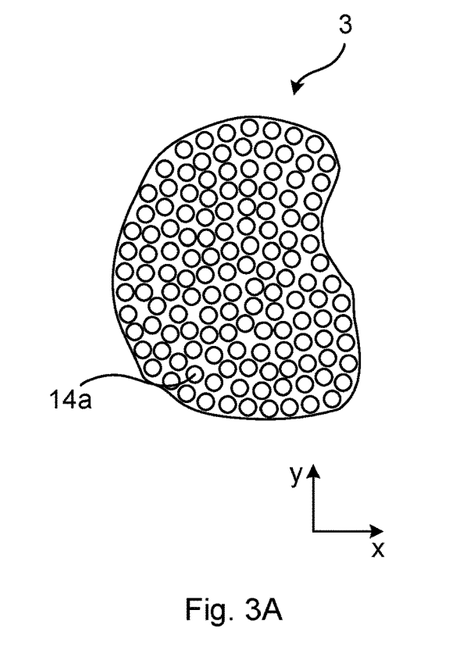
FIGS. 3A-B are schematic drawing illustrating copies of an energy layer for use in an optimization strategy.
Figure 3B:
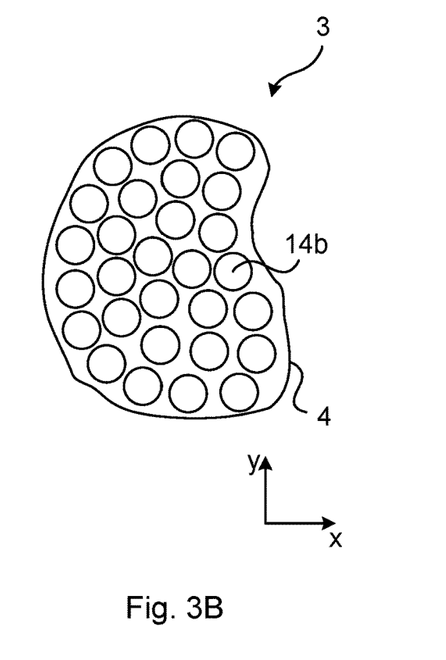

FIGS. 3A-B are schematic drawing illustrating copies of an energy layer for use in an optimization strategy. An energy layer (e.g. one of the energy layers 17a-f of FIG. 2) is shown along an x-y plane. While the energy layer does not need to be completely flat in the patient, the energy layer is here depicted as a flattened layer, as it would look if the patient were not present. The treatment planning system 1 can estimate the z position of any point of each energy layer, and can thus transform any spot between a location on the energy layer, in a flattened two dimensional space, and a location in a three dimensional space.

According to embodiments presented herein, optimization is used to provide a suitable distribution of spots of different sizes in each energy layer. As explained in more detail below, the optimization is based on copies of each energy layer where each copy is made up of different spot sizes. In this example, FIG. 3A shows a copy of an energy layer with smaller spots 14a. FIG. 3B shows a copy of the same energy layer as for FIG. 3A, but here populated with larger spots 14b. In FIGS. 3A-B, larger and smaller are here reciprocally relative terms between the two spot sizes 14a-b.

If more spot sizes were used, there would be more copies of the energy layer, such that there is one copy of the energy layer for each spot size.

While FIGS. 3A-B only disclose copies of one energy layer, there are corresponding copies for each energy layer to be used for a target volume. Furthermore, the actual spot size in the patient depends on the tissue the ion beam passes, with in general larger beam spread for high-density materials.

It is to be noted that the actual spot size also depends on the energy level: normally, the beam spread decreases with increasing energy for the same spot size setting.

Figure 4:
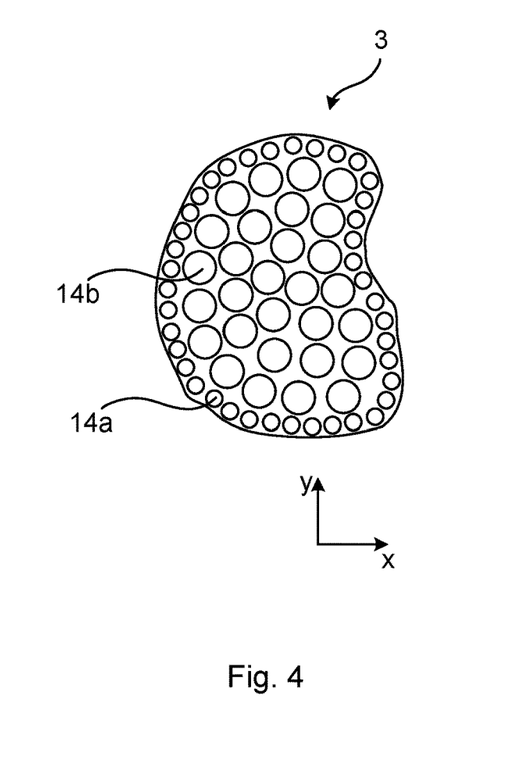
FIG. 4 is a schematic drawing illustrating a resulting energy layer after optimization has been executed.

FIG. 4 is a schematic drawing illustrating a resulting energy layer after optimization has been executed. FIG. 4 shows spots of the same energy layer which is used for FIGS. 3A-B.

In FIG. 4, the optimization has resulted in smaller spots 14a along the edge 4 of the target volume 3, while larger spots 14b are provided in the inner region of the target volume, in a central area inside the smaller spots 14a The optimized result exploits the opportunity of varying the spot size within each energy level to achieve several beneficial effects. Small spot sizes will give smaller lateral beam penumbra (i.e. lateral dose fall off outside the target volume). However, many small spots will prolong the treatment time. Hence, larger spots can be used in the central area of the target volume, since these spots will affect the beam penumbra to a smaller extent. The larger spots can result in shorter treatment time and improved robustness. Robust is here to be interpreted as robust with respect to patient setup and density estimation errors, as well as errors arising due to organ motion including any interference with the delivery, i.e. that the dose distribution is suitable even if any of these errors occur.

Optimization can be set up to gravitate towards a result such as that shown in FIG. 4 by providing suitable criteria. Such criteria can contain both a criterion to reduce penumbrae outside of the target area and a criterion to reduce treatment time.

While FIG. 4 only discloses the spot distribution of one energy layer, there are corresponding spot distributions determined for each energy layer to be used for a target volume.

Figure 5:
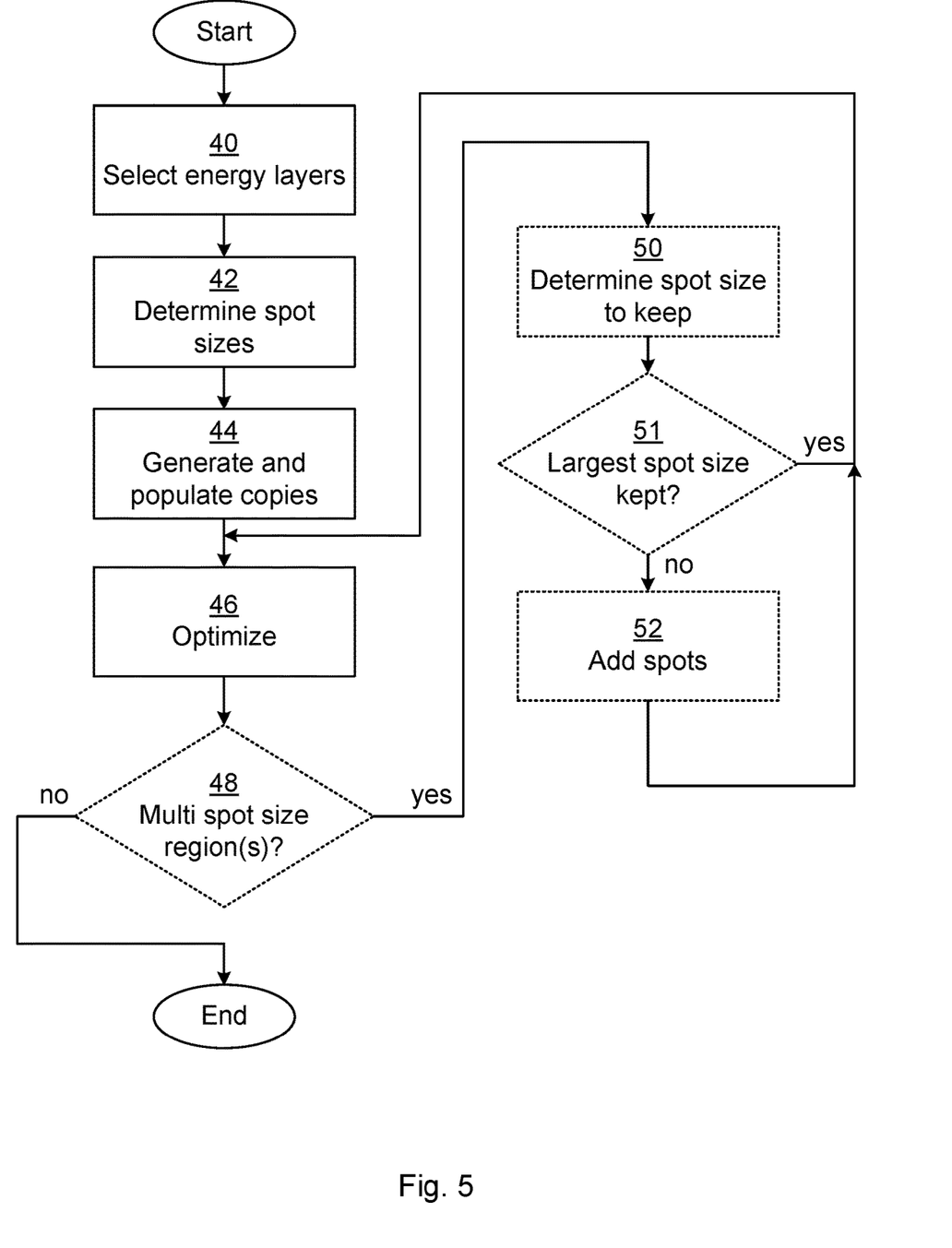
FIG. 5 is a flow chart illustrating embodiments of a method for determining a distribution of spots, the method being performed in the treatment planning system of FIG. 1.

FIG. 5 is a flow chart illustrating embodiments of a method for determining a distribution of spots, the method being performed in the treatment planning system.

As described above, the distribution of spots is intended to be used with ion beam therapy for providing the spots in a target volume. Each spot represents a collection of ions of a specific energy level and of a specific spot size at a specific lateral location.

In the following, a conditional step is a step where the method forks in two different possible paths. An optional step is a step which does not need to be performed.

In a select energy layers step 40, energy layers to be used in the treatment plan are selected. The number of energy layers depends on the target volume and the patient geometry. This results in $N_{el}$ energy layers.

In a determine spot sizes step 42, a number, greater than one, of spot sizes to use is determined. The number of spot sizes to use needs to be supported by the ion beam system which will receive the treatment plan. Any suitable number, denoted n, of spot sizes can be determined. This number can be a user parameter or it can be selected by the treatment planning system. For instance, all available spot sizes could be used. Alternatively, different spot size sets can be used for different treatment sites. For instance, treatment of head and neck could use a smaller set of spot sizes than treatment in the intestinal and pelvic region.

In a generate and populate copies step 44, the treatment planning system generates, for each energy layer, one copy of the energy layer for each spot size to use. Furthermore, each copy is populated with spots of the spot size for that copy. This is illustrated by FIGS. 3A-B and described above.

In an optimize step 46, spots of all copies of all energy layers are optimized, i.e. a total of $N_{el}*n$ energy layer copies. This optimization is achieved by repeatedly varying a weight, related to the number of ions that are delivered to the spot, of at least a subset of the spots and calculating an effect on a performance measurement, until variations of the weights fail to improve the performance measurement more than a threshold amount. The performance measurement is a scalar and will with this scheme result in at least a local optimum, where further adjustments of spot weights will not improve the end result.

The weight is related to the number of ions that are delivered to the spot and thus controls the dose amount of a spot.

The performance measurement is calculated by combining a plurality of evaluation criteria. The plurality of evaluation criteria comprises a first criterion, which improves the performance measurement when a total treatment time is reduced, and a second criterion which improves the performance measurement when a desired dose distribution in the treatment volume is achieved.

The first criterion aims at reducing the treatment time. For most ion delivery systems, there is a dead time between the delivery of spots, i.e. travel and stabilization time between consecutive spots. The largest gain in treatment time, when switching from smaller to larger spots, can be found in reducing this dead time between spots, and is thus not directly related to the spot weight (and actual delivery) of a specific spot. In the context of optimization with respect to variation of spot weights, the first criterion comprises a spot specific measure, which for each spot takes into account the dead time between the spots. Such a measure will be spot size dependent and can be directly or indirectly related to the delivery time. It can be formulated in a number of different ways, and can for example be based on any one or more of the following:

a) spot size. Larger spots as compared to smaller spots with the same energy will reduce the treatment time. This is based on the fact that for most ion beam delivery systems, it is more time efficient to deliver the dose from fewer large spots, than from more small spots, taking into account that an energy layer copy with larger spots will contain fewer spots than an energy layer copy with smaller spots. The accumulated dead time will thus be shorter for an energy layer copy with larger spots, as compared to an energy layer copy with smaller spots. The performance measurement of the optimization is in this case improved for larger spots as compared to smaller spots.

b) spot spacing. For spots with larger spot spacing (distance to nearest neighbor in the same energy layer copy), the treatment time will be reduced compared to spots with smaller spot spacing. The reason for this is that there will be fewer spots in an energy layer copy with larger spot spacing, and the accumulated dead time for the complete energy layer copy will be smaller. The performance measurement of the optimization is in this case improved for spots with larger spot spacing as compared to spots with smaller spot spacing. For treatment plans for ion beam therapy, it is beneficial to choose the initial spot spacing (also referred to as the spot spacing grid) either manually or automatically based on the actual spot size, such that the energy fluence of a layer with spots of the same energy do not display any fluctuations due to a too coarse spot spacing grid. Larger spots will allow a coarser spot spacing grid than smaller spots. The measure could be based either on the actual distance to nearest neighbor for each spot in the same energy layer copy, or on the initial spot spacing in the spot spacing grid, which is not spot dependent and the same quantity will for this alternative be assigned for all spots in the same energy layer copy.

c) delivery time of an energy layer copy. For this measure, the delivery time for each energy layer copy, including the dead time between spots, is estimated. Each spot in a specific energy layer copy will be assigned a quantity, which is directly proportional to the delivery time. As an alternative, each spot in an energy layer copy could be assigned a quantity directly proportional to the accumulated dead time between all spots in that energy layer copy. For both alternatives, the assigned quantity will be identical for all spots in the same energy layer copy. Larger spots in an energy layer copy will lead to a shorter delivery time as compared to smaller spots, due to fewer spots and shorter accumulated dead time between the spots. The performance measurement of the optimization is in this case improved for spots in an energy layer copy, where the delivery time of the energy layer copy or the accumulated dead time between spots in the energy layer copy is shorter as compared to spots in an energy layer copy with longer delivery time or accumulated dead time.

Other measures that directly or indirectly relates to the treatment time or the spot size could also be used.

The second criterion, relating to dose distribution, can be defined such that it improves the performance measurement when a penumbra outside the target volume is reduced.

In the step of optimization, the weights of the spots are, as mentioned above, repeatedly varied to improve the performance measurement. The dose distribution is directly altered by changing the weight of the spots, and there is a direct relation between the spot weights and the effect on the performance measurement for the second criterion, relating to dose distribution. For the first criterion, relating to treatment time, there is no such direct relation. The treatment time measures described above are related to dead time between delivery of the individual spots and are therefore not explicitly dependent on the spot weights. However, since the optimization is performed with respect to the spot weights, an artificial relation between the spot weights and treatment time measures is established, such that the performance measurement related to the first criterion is improved when the spot weight is increased for spots with a favorable measure (large spot size, large spot distance, short delivery time). When basing the first criterion on the spot size, this can for example be achieved in the optimization by penalizing high spot weights for spots with smaller spot sizes, which in turn will favor higher spot weights for spots with larger spot sizes.

The first criterion and the second criterion are balancing criteria. If the first criterion (relating to delivery time) would not form part of the performance measurement, the optimization may result in the smallest spot sizes in each energy layer, resulting in an excessive delivery time. On the other hand, if the second criterion (relating to dose distribution) would not form part of the performance measurement, the optimization may result in the largest spot sizes in each energy layer, which may not provide appropriate dose distribution.

In a final action of the optimize step 46, a spot filtering is performed. The spot filtering will remove spots with weights below a certain threshold value, which can be set by the user or directly by the system based on the capabilities of the ion delivery system.

In an optional conditional multi spot size region(s) step 48, the treatment planning system determines whether it can find any multi spot size region of a single energy layer which is covered by spots of different sizes of respective copies of the energy layer. A multi spot size region could for example be the size of the largest spot. If any such multi spot size regions are found, the method proceeds to an optional determine spot size to keep step 50. Otherwise, the method ends.

In the optional determine spot size to keep step 50, the treatment planning system determines, in each multi spot size region, which single spot size to keep. The spots of other spot sizes in the multi spot size region are removed, i.e. their weights are set to zero. By reducing spots of a multi spot size region to spots of a single size, the delivery time is reduced. The method to determine which spot sizes to keep could for example be based on the spot size, the total spot fluence for each spot size, or the accumulated weight of the spots, or a combination of these parameters.

Optionally, the determination of what spots to keep is based on a user parameter.

In an optional conditional largest spot size kept step 51, the treatment planning system determines whether the spot size to keep, in a particular multi spot size region, is the largest spot size in the multi spot size region. If this is the case, the method returns to the optimize step 46. Otherwise, the method proceeds to an optional add spots step 52.

In the optional add spots step 52, the treatment planning system adds, in each multi spot size region, spots of the spot size to keep, to improve coverage. This may need to be done when larger spots in the multi spot size region have been removed, since the larger spots have better coverage. After this step, the method returns to the optimize step 46.

This method could be applied in both continuous scanning (line scanning) and in discrete spot scanning (step-and-shoot spot scanning). The spot sizes could vary both within a continuous range and in discrete steps.

Figure 6:
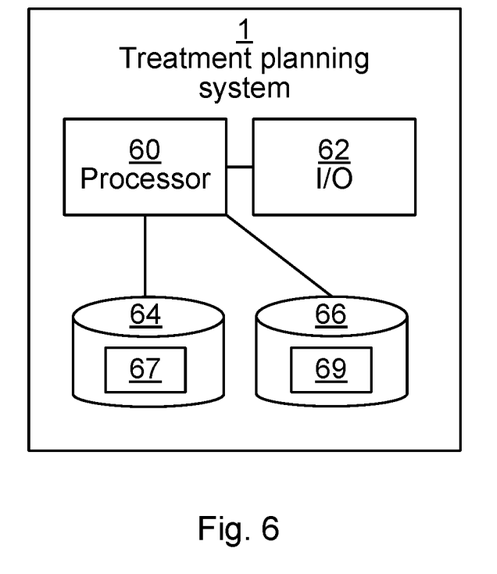
FIG. 6 is a schematic diagram illustrating components of the treatment planning system of FIG. 1 according to one embodiment.

FIG. 6 is a schematic diagram illustrating components of the treatment planning system 1 of FIG. 1 according to one embodiment. A processor 6o is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIG. 5 above.

The memory 64 can be any combination of random access memory (RAM) and read only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of random access memory (RAM) and read only memory (ROM). The data memory 66 can e.g. contain spot size distributions 69.

The treatment planning system 1 further comprises an I/O interface 62 for communicating with other external entities. Optionally, the I/O interface 62 also includes a user interface.

Other components of the treatment planning system 1 are omitted in order not to obscure the concepts presented herein.

Figure 7:
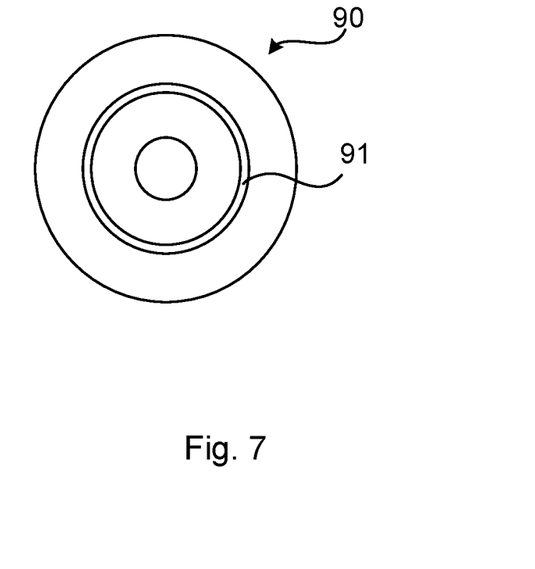
FIG. 7 shows one example of a computer program product comprising computer readable means.

FIG. 7 shows one example of a computer program product comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 6. While the computer program 91 is here schematically shown as a track on the depicted optical disk, the computer program can be stored in any way which is suitable for the computer program product, such as a removable solid state memory, e.g. a Universal Serial Bus (USB) drive.

Here now follows a list of embodiments from another perspective, enumerated with roman numerals.

i. A method for determining a treatment plan comprising a distribution of spots of varying sizes for use with ion beam therapy for providing the spots in a target volume, wherein each spot represents a collection of ions of a specific energy and of a specific spot size at a specific lateral location, the method being performed in a treatment planning system and comprising the steps of:

selecting energy layers to be used in the treatment plan;

determining a number, greater than one, of spot sizes to use;

generating, for each energy layer, one copy for each spot size to use and populating each copy with spots of the spot size for that copy; and optimizing spots of all copies of all energy layers, by repeatedly varying a weight of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved.

ii. The method according to embodiment i, wherein the step of optimizing comprises performing a spot filtering to remove spots with weights below a threshold value.

iii. The method according to embodiment i or ii, further comprising the step, after the step of optimizing spots, of:

finding any multi spot size region of a single energy layer which is covered by spots of different sizes;

determining, in each multi spot size region, which single spot size to keep and removing the spots of other spot sizes in the multi spot size region; and returning to the step of optimizing spots.

iv. The method according to embodiment iii, further comprising the step, after the step of determining which spot size to keep, of:

adding, in each multi spot size region when the spot size to keep is not the largest spot size in the multi spot size region, spots of the spot size to keep, to improve coverage.

v. The method according to embodiment iii or iv, wherein the step of determining which spot size to keep comprises determining to keep a spot size according to a user parameter.

vi. The method according to any of the preceding embodiments, wherein the second criterion improves the performance measurement when a penumbra outside the target volume is reduced.

vii. A treatment planning system for determining a treatment plan comprising a distribution of spots of varying sizes for use with ion beam therapy for providing the spots in a target volume, wherein each spot represents a collection of ions of a specific energy level and of a specific spot size at a specific lateral location, the treatment planning system comprising:
 a processor; and
 a memory storing instructions that, when executed by the processor, cause the treatment planning system to:
 select energy layers to be used in the treatment plan;
 determine a number, greater than one, of spot sizes to use;
 generate, for each energy layer, one copy for each spot size to use and populating each copy with spots of the spot size for that copy; and
 optimize spots of all copies of all energy layers, by repeatedly varying a weight of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved.

viii. The treatment planning system according to embodiment vii, further comprising instructions that, when executed by the processor, cause the treatment planning system to:
 find any multi spot size region of a single energy layer which is covered by spots of different sizes;
 determine, in each multi spot size region, which single spot size to keep and removing the spots of other spot sizes in the multi spot size region; and
 return to the instructions to optimize spots.

ix. The treatment planning system according to embodiment viii, further comprising instructions that, when executed by the processor, cause the treatment planning system to:
 add, in each multi spot size region when the spot size to keep is not the largest spot size in the multi spot size region, spots of the spot size to keep, to improve coverage.

x. The treatment planning system according to embodiment viii or ix, wherein the instructions to determine, which spot size to keep comprise instructions that, when executed by the processor, cause the treatment planning system to determine to keep a spot size according to a user parameter.

xi. The treatment planning system according to any of embodiments vii to x, wherein the second criterion improves the performance measurement when a penumbra outside the target volume is reduced.

xii. A treatment planning system for determining a treatment plan comprising a distribution of spots of varying sizes for use with ion beam therapy for providing the spots in a target volume, wherein each spot represents a collection of ions of a specific energy level and of a specific spot size at a specific lateral location, the treatment planning system comprising:
 means for selecting energy layers to be used in the treatment plan;
 means for determining a number, greater than one, of spot sizes to use;
 means for generating, for each energy layer, one copy for each spot size to use and populating each copy with spots of the spot size for that copy; and
 means for optimizing spots of all copies of all energy layers, by repeatedly varying a weight of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved.

xiii. A computer program for determining a treatment plan comprising a distribution of spots for use with ion beam therapy for providing the spots in a target volume, wherein each spot represents a collection of ions of a specific energy level and of a specific spot size at a specific lateral location, the computer program comprising computer program code which, when run on a treatment planning system causes the treatment planning system to:
 select energy layers to be used in the treatment plan;
 determine a number, greater than one, of spot sizes to use;
 generate, for each energy layer, one copy for each spot size to use and populating each copy with spots of the spot size for that copy; and
 optimize spots of all copies of all energy layers, by repeatedly varying a weight of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved.

xiv. A computer program product comprising a computer program according to embodiment xiii and a computer readable means on which the computer program is stored.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method for determining a treatment plan comprising a distribution of spots of varying sizes for use with ion beam therapy for providing the spots in a target volume, wherein each spot represents a collection of ions of a specific energy and of a specific spot size at a specific lateral location, the method being performed in a treatment planning system and comprising the steps of:

selecting energy layers to be used in the treatment plan;

determining a number, greater than one, of spot sizes to use;

generating, for each energy layer, one copy of the energy layer for each spot size to use, and populating each copy with spots of the spot size for that copy; and optimizing spots of all copies of all energy layers, by repeatedly varying a weight, related to the number of ions that are delivered to the spot, of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved, wherein the second criterion improves the performance measurement when a penumbra outside the target volume is reduced, and wherein the treatment plan is provided to an apparatus configured to apply the treatment plan to a patient.

2. The method according to claim 1, wherein the step of optimizing comprises performing a spot filtering to remove spots with weights below a threshold value.

3. The method according to claim 1, further comprising the step, after the step of optimizing spots, of:

finding any multi spot size region of a single energy layer which is covered by spots of different sizes of respective copies of the energy layer;

determining, in each multi spot size region, Which single spot size to keep and removing the spots of other spot sizes in the multi spot size region; and returning to the step of optimizing spots.

4. The method according to claim 3, further comprising the step, after the step of determining which spot size to keep, of:

adding, in each multi spot size region when the spot size to keep is not the largest spot size in the multi spot size region, spots of the spot size to keep, to improve coverage.

5. The method according to claim 3, wherein the step of determining which spot size to keep comprises determining to keep a spot size according to a user parameter.

6. A treatment planning system for determining a treatment plan comprising a distribution of spots of varying sizes for use with ion beam therapy for providing the spots in a target volume, wherein each spot represents a collection of ions of a specific energy level and of a specific spot size at a specific lateral location, the treatment planning system comprising:

a processor; and a memory storing instructions that, when executed by the processor, cause the treatment planning system to:

select energy layers to be used in the treatment plan;

determine a number, greater than one, of spot sizes to use;

generate, for each energy layer, one copy of the energy layer for each spot size to use and populating each copy with spots of the spot size for that copy; and optimize spots of all copies of all energy layers, by repeatedly varying a weight, related to the number of ions that are delivered to the spot, of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved, wherein the second criterion improves the performance measurement when a penumbra outside the target volume is reduced, and wherein the treatment plan is provided to an apparatus configured to apply the treatment plan to a patient.

7. The treatment planning system according to claim 6, further comprising instructions that, when executed by the processor, cause the treatment planning system to:

find any multi spot size region of a single energy layer which is covered by spots of different sizes of respective copies of the energy layer;

determine, in each multi spot size region, which single spot size to keep and removing the spots of other spot sizes in the multi spot size region; and return to the instructions to optimize spots.

8. The treatment planning system according to claim 7, further comprising instructions that, when executed by the processor, cause the treatment planning system to:

add, in each multi spot size region when the spot size to keep is not the largest spot size in the multi spot size region, spots of the spot size to keep, to improve coverage.

9. The treatment planning system according to claim 7, wherein the instructions to determine, which spot size to keep comprise instructions that, when executed by the processor, cause the treatment planning system to determine to keep a spot size according to a user parameter.

10. A treatment planning system for determining a treatment plan comprising a distribution of spots of varying sizes for use with ion beam therapy for providing the spots in a target volume, wherein each spot represents a collection of ions of a specific energy level and of a specific spot size at a specific lateral location, the treatment planning system comprising:

means for selecting energy layers to be used in the treatment plan;

means for determining a number, greater than one, of spot sizes to use;

means for generating, for each energy layer, one copy of the energy layer for each spot size to use and populating each copy with spots of the spot size for that copy; and means for optimizing spots of all copies of all energy layers, by repeatedly varying a weight, related to the number of ions that are delivered to the spot, of at least a subset of the spots and calculating an effect on a performance measurement, until variations of the weights fail to improve the performance measurement more than a threshold amount, wherein the performance measurement is calculated by combining a plurality of evaluation criteria, wherein the plurality of evaluation criteria comprises a first criterion which improves the performance measurement when a total treatment time is reduced and a second criterion which improves the performance measurement when a desired dose distribution in the treatment volume is achieved, wherein the second criterion improves the performance measurement when a penumbra outside the target volume is reduced, and wherein the treatment plan is provided to an apparatus configured to apply the treatment plan to a patient.

11. A non-transitory computer readable medium having a computer program that when executed on a computer causes the computer to perform the method of claim 1.

* * * * *